United States Patent
Lee et al.

(10) Patent No.: US 10,301,281 B2
(45) Date of Patent: May 28, 2019

(54) CRYSTAL FORMS OF A CCR5 ANTAGONIST

(71) Applicants: Merck Sharp & Dohme Corp., Rahway, NJ (US); Merck Sharp & Dohme B.V., Oss (NL)

(72) Inventors: Alfred Y. Lee, Robbinsville, NJ (US); William De Wildt, Wijchen (NL)

(73) Assignees: MERCK SHARP & DOHME CORP., Rahway, NJ (US); MERCK SHARP & DOHME B.V. (NL)

( * ) Notice: Subject to any disclaimer, the term of this patent is extended or adjusted under 35 U.S.C. 154(b) by 0 days.

(21) Appl. No.: 15/534,541

(22) PCT Filed: Nov. 11, 2015

(86) PCT No.: PCT/US2015/060051
§ 371 (c)(1),
(2) Date: Jun. 9, 2017

(87) PCT Pub. No.: WO2016/094011
PCT Pub. Date: Jun. 16, 2016

(65) Prior Publication Data
US 2017/0342053 A1    Nov. 30, 2017

Related U.S. Application Data

(63) Continuation of application No. 62/090,710, filed on Dec. 11, 2014.

(51) Int. Cl.
C07D 401/14 (2006.01)
A61K 31/496 (2006.01)
C07D 401/06 (2006.01)

(52) U.S. Cl.
CPC ......... *C07D 401/14* (2013.01); *C07D 401/06* (2013.01)

(58) Field of Classification Search
CPC .................................................. C07D 401/14
See application file for complete search history.

(56) References Cited

U.S. PATENT DOCUMENTS

| | | | |
|---|---|---|---|
| 6,391,865 | B1 | 5/2002 | Baroudy et al. |
| 7,014,866 | B2 | 3/2006 | Infeld et al. |
| 7,592,459 | B2 | 9/2009 | Arad et al. |
| 7,825,121 | B2 | 11/2010 | Ramanathan et al. |
| 2009/0270336 | A1 | 10/2009 | Liu et al. |
| 2016/0296467 | A1 | 10/2016 | Aarts et al. |

FOREIGN PATENT DOCUMENTS

WO    WO2012151165 A1    11/2012

OTHER PUBLICATIONS

Hu et al., Blockade of Attachment and Fusion Receptors Inhibits HIV-1 Infection of Human Cervical Tissue, The Journal of Experimental Medicine, 2004, pp. 1065-1075, vol. 199, No. 8.
Lederman et al., Prevention of Vaginal SHIV Transmission in Rhesus Macaques Through Inhibition of CCR5, Science, 2004, pp. 485-487, V0l. 306.
National Center for Biotechnology Information. PubChem Compound Database; CID=3009355, https://pubchem.ncbi.nlm.nih.gov/compound/3009355 (accessed Jun. 8, 2017).

*Primary Examiner* — Emily A Bernhardt
(74) *Attorney, Agent, or Firm* — Carol S. Quagliato; John C. Todaro

(57) ABSTRACT

The present disclosure relates to forms of a CCR5 inhibitory compound, (4,6-dimethylpyrimidin-5-yl)(4-((3S)-4-((1R)-2-methoxy-1-(4-(trifluoromethyl)phenyl)ethyl)-3-methylpiperazin-1-yl)-4-methylpiperidin-1-yl)methanone.

16 Claims, 3 Drawing Sheets

CRYSTAL FORMS OF A CCR5 ANTAGONIST

CROSS-REFERENCE TO RELATED APPLICATIONS

This application is a National Stage application of International Patent Application No. PCT/US2015/060051, filed Nov. 11, 2015, which claims priority to U.S. Provisional Patent Application No. 62/090,710, filed Dec. 11, 2014.

FIELD OF THE INVENTION

The present invention relates to different forms of a CCR5 antagonist compound. CCR5 antagonist compounds may have therapeutic and research applications, in particular to the prevention of the transmission of HIV and for the prevention of AIDS.

BACKGROUND OF THE INVENTION

The global health crisis caused by HIV, the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

HIV typically establishes an infection by first attaching to CD4 receptors on white blood cells and then grabbing a second receptor known as CC Chemokine Receptor 5 ("CCR5"), which normally responds to immune chemicals called chemokines. Epidemiological and viral transmission studies have shown that viruses using the CCR5 receptor are often associated with transmission of HIV infection between individuals. Therefore, blocking these viruses by prophylactic treatment with a specific CCR5 inhibitor should prove an effective way to prevent HIV transmission in a susceptible population. For example, M. Lederman et al., *Prevention of Vaginal SHIV Transmission in Rhesus Macaques Through Inhibition of CCR5*, SCIENCE 306, 485-487 (Oct. 15, 2004), describe a study of the ability of $N^{\alpha}$-(n-nonanoyl)-des-Ser$^1$-[L-thioproline$^2$, L-α-cyclohexyl-glycine$^3$] RANTES ("PSC-RANTES") to prevent acquisition of SHIV infection at a mucosal skin. Q. Hu et al., *Blockade of Attachment and Fusion Receptors Inhibits HIV-1 Infection of Human Cervical Tissue*, 199(8) J. EXP. MED. 1065-1075 (Apr. 19, 2004), describe the blockade of the effect of both CCR5 and CXCR4 to prevent infection.

The present invention relates to small molecules that are CCR5 antagonists, in particular, Compound A, (4,6-dimethylpyrimidin-5-yl)(4-((3 S)-4-((1R)-2-methoxy-1-(4-(trifluoromethyl)phenyl)ethyl)-3-methylpiperazin-1-yl)-4-methylpiperidin-1-yl)methanone, or a pharmaceutically salt thereof, which is disclosed in Baroudy et al., U.S. Pat. No. 6,391,865, incorporated herein by reference.

Compound A

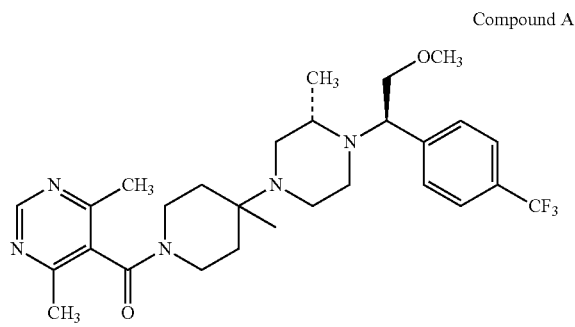 [SMILES: COC[C@@H](c1ccc(C(F)(F)F)cc1)N1CCN(C2(C)CCN(C(=O)c3c(C)ncnc3C)CC2)C[C@@H]1C]

U.S. Pat. No. 6,391,865 discloses novel antagonists of the CCR5 receptor that are useful for the treatment of AIDS and related HIV infections, including Compound A. CCR5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Different forms—amorphous, solvate, and crystalline—of CCR5 antagonist compounds can provide different properties of stability, solubility, dissolution rate, hardness, compressibility and melting point, as well as other physical and mechanical properties. Such physical and mechanical properties can affect the ease of manufacture, formulation, storage and transport of the CCR5 antagonist compounds. Thus, there is a need for identification of new forms of CCR5 antagonist compounds and ways for preparing such forms.

SUMMARY OF THE INVENTION

The present invention includes different forms of Compound A, (4,6-dimethylpyrimidin-5-yl)(4-((3 S)-4-((1R)-2-methoxy-1-(4-(trifluoromethyl)phenyl)ethyl)-3-methylpiperazin-1-yl)-4-methylpiperidin-1-yl)methanone, or a pharmaceutically salt thereof:

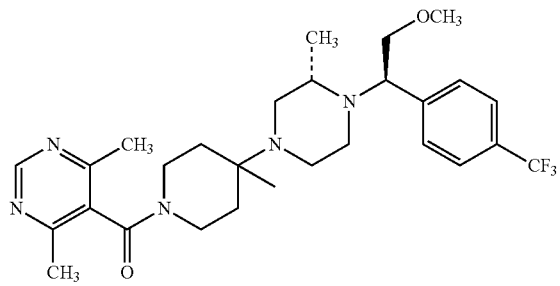 [SMILES: COC[C@@H](c1ccc(C(F)(F)F)cc1)N1CCN(C2(C)CCN(C(=O)c3c(C)ncnc3C)CC2)C[C@@H]1C]

Aspects of the present invention directed to amorphous forms of Compound A, a crystalline tert-butanol solvate of Compound A, and/or crystalline anhydrate Form I of Compound A include a pharmaceutical composition comprising a therapeutically effective amount of amorphous forms of Compound A, a crystalline tert-butanol solvate of Compound A, and/or crystalline anhydrate Form I of Compound A and a pharmaceutically acceptable carrier; treating an HIV-infected patient with the compound; use of amorphous forms of Compound A, a crystalline tert-butanol solvate of Compound A, and/or crystalline anhydrate Form I of Compound A in medicine; the preparation of a medicament for use in treating HIV in a patient; and methods of making amorphous forms of Compound A, a crystalline tert-butanol solvate of Compound A, and/or crystalline anhydrate Form I of Compound A.

Other embodiments, aspects and features of the present invention are either further described herein or will be apparent from the ensuing description, examples and appended claims.

DETAILED DESCRIPTION OF THE INVENTION

CCR5 antagonist compounds able to inhibit HIV transmission have different potential uses including preventing HIV transmission between individuals. The ability to prevent or inhibit HIV transmission can be used for prophylactic and therapeutic applications. Compound A is a CCR5 antagonist compound, an inhibitor of HIV transmission, which is useful in the prevention of transmission of HIV.

Compound A Forms

Three different Compound A forms were identified, an amorphous free base form, a crystalline tert-butanol solvate form (Solvate I), and a crystalline anhydrate form (Form I). Of these, Form I is the most stable and desirable form.

Figure 1:
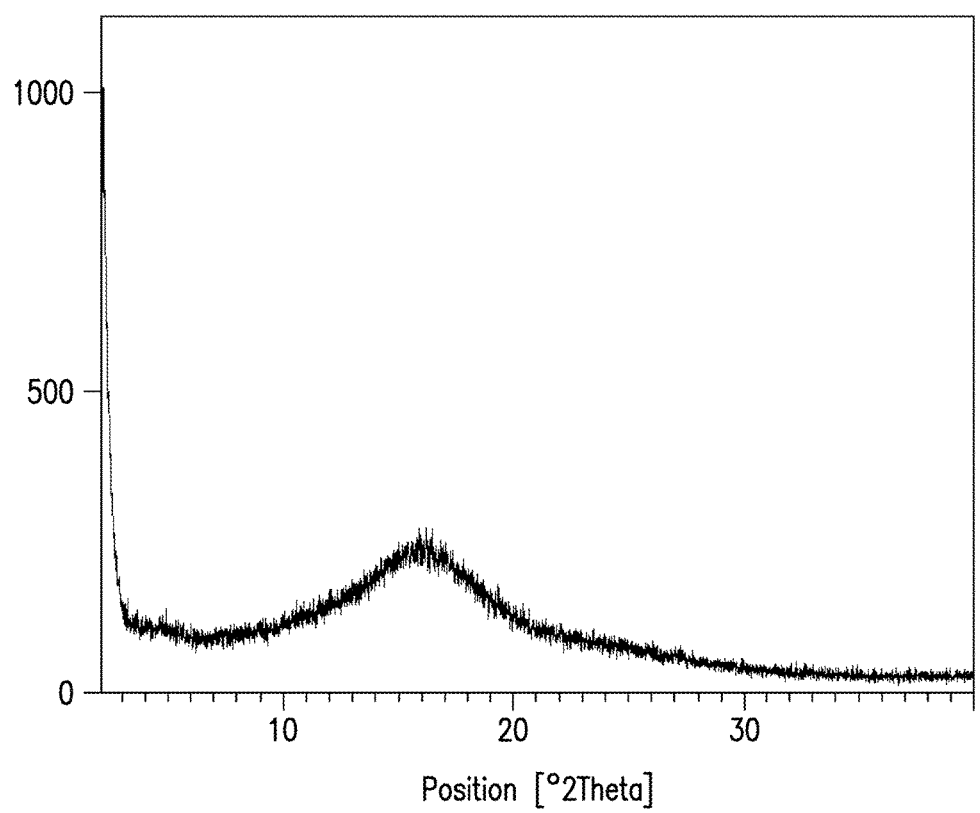
FIG. 1 provides a characteristic X-ray diffraction pattern for the amorphous free base form of Compound A of Example 1.

A first embodiment is directed to the amorphous free base form of Compound A. The amorphous free base form is characterized by an X-ray powder diffraction pattern obtained using copper $K_\alpha$ radiation (i.e., the radiation source is a combination of Cu $K_{\alpha 1}$ and $K_{\alpha 2}$ radiation), which is illustrated in FIG. 1.

Figure 2:
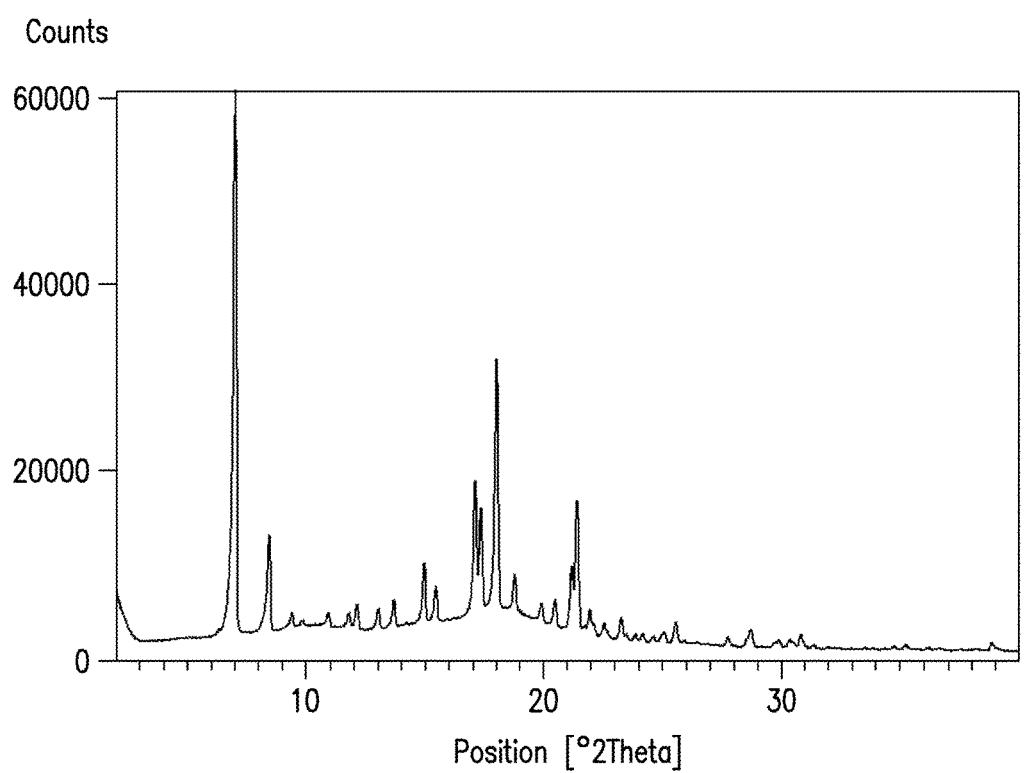
FIG. 2 provides a characteristic X-ray diffraction pattern for the crystalline tert-butanol solvate form of Compound A of Example 2.

A second embodiment is directed to a crystalline tert-butanol solvate of Compound A, Solvate I. Solvate I is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 2.

In a first aspect of the second embodiment, Solvate I is characterized by an X-ray powder diffraction pattern obtained using copper $K_\alpha$ radiation, which comprises 2Θ values (i.e., reflections at 2Θ values) in degrees of about 8.48, 9.39, and 17.10.

Reference to "about" with respect to 2Θ values provided herein indicates ±0.1. In this embodiment and analogous embodiments that follow, the term "about" is understood to modify each of the 2Θ values; e.g., the expression "about 8.48, 9.39, and 17.10" is short-hand for "about 8.48, about 9.39, and about 17.10".

In a second aspect of the second embodiment, Solvate I is characterized by an X-ray powder diffraction pattern obtained using copper $K_\alpha$ radiation, which comprises 2Θ values in degrees of about 7.06, 8.48, 9.39, 14.97, 17.10, 17.34, 17.99, 18.78, 21.17, and 21.42.

In a third aspect of the second embodiment, Solvate I is characterized by an X-ray powder diffraction pattern obtained using copper $K_\alpha$ radiation, which comprises 2Θ values in degrees of about 7.06, 8.48, 9.39, 13.70, 14.97, 15.45, 17.10, 17.34, 17.99, 18.78, 19.90, 20.47, 21.17, and 21.42.

In a fourth aspect of the second embodiment, Solvate I is characterized by an X-ray powder diffraction pattern obtained using copper $K_\alpha$ radiation, which comprises 2Θ values in degrees of about 7.06, 8.48, 9.39, 10.94, 11.81, 12.15, 13.06, 13.70, 14.97, 15.45, 17.10, 17.34, 17.99, 18.78, 19.90, 20.47, 21.17, 21.42, 21.93, 23.24 and 25.53.

In a fifth embodiment, Solvate I is substantially pure. Reference to "substantially pure" means the particular form makes up at least 50% of the compound present. In different embodiments, Solvate I is at least 75%, at least 85%, at least 90%, at least 95%, or about 94%-99% of the total amount of Compound A present.

Figure 3:
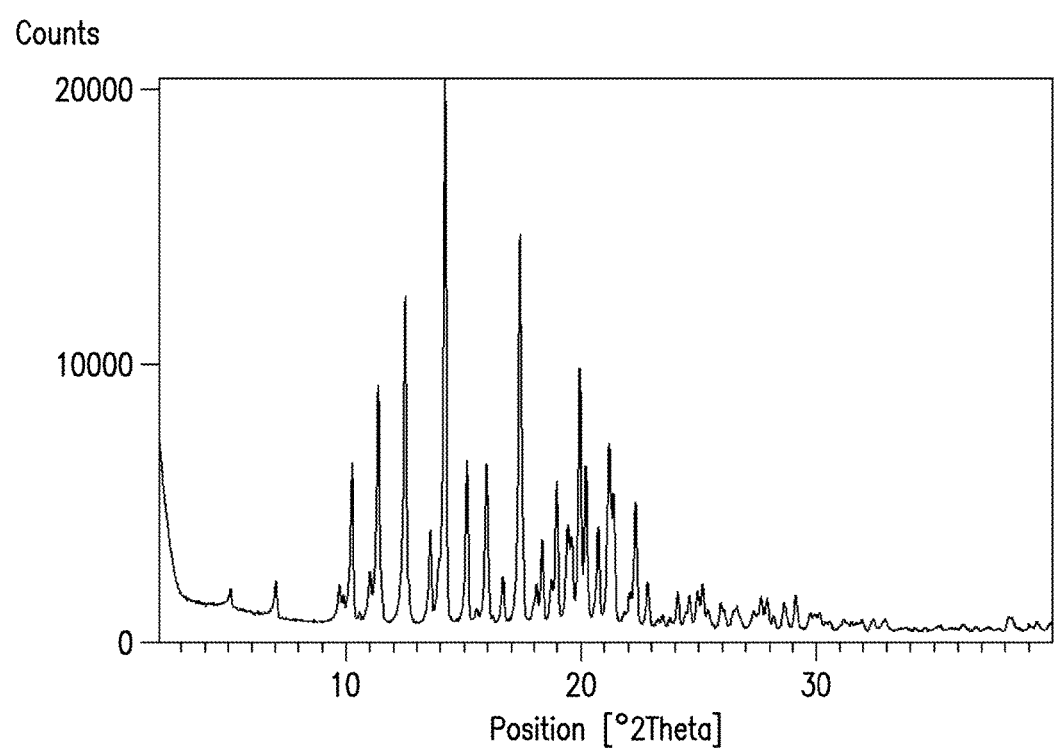
FIG. 3 provides a characteristic X-ray diffraction pattern for the crystalline anhydrate Form I of Compound A of Example 3.

A third embodiment is directed to a crystalline anhydrate form of Compound A, Form I. Form I is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peeks are illustrated in FIG. 3.

In a first aspect of the third embodiment, Form I is characterized by an X-ray powder diffraction pattern obtained using copper $K_\alpha$ radiation, which comprises 2Θ values in degrees of about 5.06, 10.24, and 14.17.

In a second aspect of the third embodiment, Form I is characterized by an X-ray powder diffraction pattern obtained using copper $K_\alpha$ radiation, which comprises 2Θ values in degrees of about 5.06, 10.24, 11.34, 12.48, 14.17, 17.33, 19.90, and 21.14.

In a third aspect of the third embodiment, Form I is characterized by an X-ray powder diffraction pattern obtained using copper $K_\alpha$ radiation, which comprises 2Θ values in degrees of about 5.06, 10.24, 11.34, 12.48, 13.55, 14.17, 15.10, 15.93, 17.33, 18.32, 18.93, 19.41, 19.57, 19.90, 20.15, 20.69, 21.14, 21.35, and 22.27.

In a fourth aspect of the third embodiment, Form I is characterized by an X-ray powder diffraction pattern obtained using copper $K_\alpha$ radiation, which comprises 2Θ values in degrees of about 5.06, 7.01, 9.69, 9.85, 10.24, 10.99, 11.34, 12.48, 13.55, 13.89, 14.17, 15.10, 15.93, 16.62, 17.33, 18.07, 18.32, 18.68, 18.93, 19.41, 19.57, 19.90, 20.15, 20.69, 21.14, 21.35, 22.00, 22.27, 22.77, 24.05, 24.55, 24.88, 25.10, 27.58, and 27.84.

In a fifth embodiment, Form I is substantially pure. In different embodiments, Form I makes up at least 75%, at least 85%, at least 90%, at least 95%, or about 94%-99% of Compound A present.

Isotopic Enrichment

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds described herein can be prepared without undue experimentation by conventional techniques well known to those skilled in the art or by processes analogous to those described in the Schemes and Examples provided herein using appropriate isotopically-enriched reagents and/or intermediates.

Administration and Compositions

As used herein, the term "composition" is intended to encompass a product comprising the specified ingredients, as well as any product which results, directly or indirectly, from combining the specified ingredients.

By "pharmaceutically acceptable" is meant the ingredients of the pharmaceutical composition are compatible with each other and are suitable to the recipient thereof.

The term "subject" (alternatively referred to herein as "patient") as used herein refers to an animal, preferably a mammal, most preferably a human, who is the object of treatment, observation or experiment.

The term "effective amount" indicates a sufficient amount to exert a therapeutic or prophylactic effect. For a patient not infected with HIV, an effective amount is sufficient to achieve one or more of the following: a reduced susceptibility to HIV infection, and a reduced ability of the infecting virus to establish persistent infection for chronic disease.

Compounds can, for example, be administered by one or more of the following routes: orally, parenterally (including subcutaneous injections, intravenous, intramuscular, intrasternal injection or infusion techniques), by inhalation (such as in a spray form), transvaginally (such as in a vaginal ring delivery system), or rectally, in the form of a unit dosage of a pharmaceutical composition containing an effective amount of the compound and pharmaceutically-acceptable carrier (e.g., a carrier suitable for administration to a human patient), adjuvants and vehicles. Liquid preparations suitable for oral administration (e.g., suspensions, syrups, elixirs and the like) can employ media such as water, glycols, oils, alcohols and the like. Solid preparations suitable for oral administration (e.g., powders, pills, capsules and tablets) can employ solid excipients as such starches, sugars, kaolin, lubricants, binders, disintegrating agents and the like. Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, 21$^{th}$ edition (Lippincott Williams & Wilkins, 2006).

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the CCR5 antagonist compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimen of the CCR5 antagonist compounds of the invention and/or the pharmaceutically acceptable salts thereof will be determined by attending clinician in view of the approved doses and dosage regimen in the package insert or as set forth in the protocol taking into consideration the age, sex and condition of the patient and the severity of the HIV-1 infection.

An "anti-HIV agent" is any agent that is directly or indirectly effective in the inhibition of HIV reverse transcriptase or another enzyme required for HIV replication or infection, the or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. Suitable antiviral agents for use in combination with the disclosed forms of Compound A include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

In Table A above, EI means entry inhibitor; FI means fusion inhibitor; InI means integrase inhibitor; PI means protease inhibitor; nRTI means nucleoside reverse transcriptase inhibitor; and nnRTI means non-nucleoside reverse transcriptase inhibitor.

Drugs listed in the table can be used in a salt form.

The doses and dosage regimen of the above anti-HIV agents will be determined by attending clinician in view of the approved doses and dosage regimen in the package insert or as set forth in the protocol taking into consideration the age, sex and condition of the patient and the severity of the HIV-1 infection.

It is understood that the scope of combinations of the compounds of this invention with anti-HIV agents is not limited to the HIV antivirals listed in Table A, but includes in principle any combination with any pharmaceutical composition useful for the treatment or prophylaxis of HIV and/or AIDS. The HIV antiviral agents and other agents will typically be employed in these combinations in their conventional dosage ranges and regimens as reported in the art, including, for example, the dosages described in editions of the *Physicians' Desk Reference*, such as the 63$^{rd}$ edition (2009) and earlier editions. The dosage ranges for a compound of the invention in these combinations can be the same as those set forth above.

For preparing pharmaceutical compositions of the CCR5 antagonist compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The CCR5 antagonist compounds of the invention may also be deliverable transdermally. The transdermal compositions can take the form of creams, lotions, aerosols and/or emulsions and can be included in a transdermal patch of the matrix or reservoir type as are conventional in the art for this purpose.

Vaginal ring delivery systems, such as that described in U.S. Provisional Patent Application No. 61/914,438 (filed Dec. 11, 2013), may include a core comprising a first thermoplastic polymer and a first therapeutic agent, wherein the first therapeutic agent is dissolved in the first thermoplastic polymer, and a skin surrounding the core comprising a second thermoplastic polymer and a second therapeutic agent, wherein the second therapeutic agent is in solid form, and the first therapeutic agent and the second therapeutic agent may be the same or different.

Other embodiments of the present invention include the following:

(a) A pharmaceutical composition comprising an effective amount of the disclosed forms of Compound A and a pharmaceutically acceptable carrier.

(b) The pharmaceutical composition of (a), further comprising a second therapeutic agent selected from the group consisting of anti-HIV agents.

(c) The pharmaceutical composition of (b), wherein the anti-HIV agents is an antiviral selected from the group consisting of entry inhibitors, fusion inhibitors, integrase inhibitors, protease inhibitors, nucleoside reverse transcriptase inhibitors, and non-nucleoside reverse transcriptase inhibitors.

(d) A pharmaceutical combination that is (i) the disclosed forms of Compound A and (ii) a second therapeutic agent selected from the group consisting of anti-HIV agents; wherein the disclosed forms of Compound A and the second therapeutic agent are each employed in an amount that renders the combination effective for preventing the transmission of HIV.

(e) The combination of (d), wherein the anti-HIV agents is an antiviral selected from the group consisting of entry inhibitors, fusion inhibitors, integrase inhibitors, protease inhibitors, nucleoside reverse transcriptase inhibitors, and non-nucleoside reverse transcriptase inhibitors.

(f) A method of inhibiting HIV transmission in a subject in need thereof, which comprises administering to the subject an effective amount of the disclosed forms of Compound° A.

(g) A method of inhibiting HIV transmission in a subject in need thereof, which comprises administering to the subject the pharmaceutical composition of (a), (b) or (c) or the combination of (d) or (e).

The present invention also includes a compound of the present invention for use in medicine; or for use in (i) a medicament, (ii) in the preparation of a medicament, for inhibiting HIV transmission. In these uses, the compounds of the present invention can optionally be employed in combination with one or more second therapeutic agents selected from anti-HIV agents.

X-ray powder diffraction studies are widely used to characterize crystallinity, and polymorphism. The X-ray powder diffraction patterns disclosed herein were generated on a Philips Analytical X'Pert PRO X-ray Diffraction System with PW3040/60 console. A PW3373/00 ceramic Cu LEF X-ray tube K-Alpha radiation was used as the source.

EXAMPLES

Abbreviations

MeOH Methanol, CH$_3$OH
NaOH Sodium hydroxide
DCM Dichloromethane, CH$_2$Cl$_2$
tBuOH tert-Butanol, C(CH$_3$)$_3$OH Example 1: Amorphous Compound A Free Base

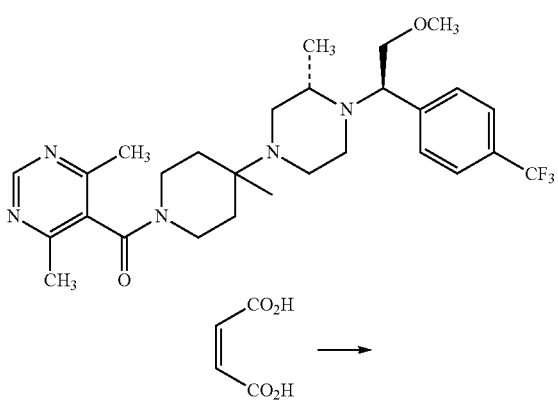

-continued

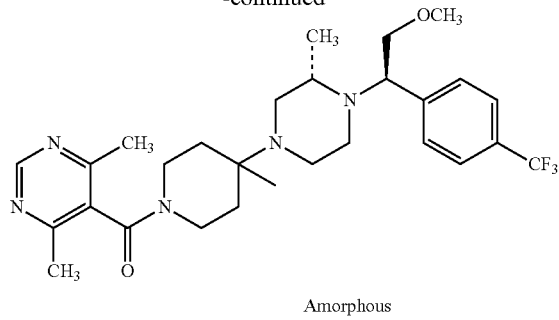

Amorphous

The maleate salt of Compound A (obtained according to the procedures of U.S. Pat. No. 6,943,251, Example 10) was converted into the free base by employing NaOH in DCM. The oily material was evaporated to a gum and dried for several days at 50° C. yielding amorphous solids. The de-salted amorphous substance was milled using a mortar and pestle to provide powder material.

An X-ray powder diffraction pattern was generated to characterize Compound A amorphous free base form. The pattern is shown in FIG. 1.

Example 2: Compound A Free Base Tert-Butanol Solvate

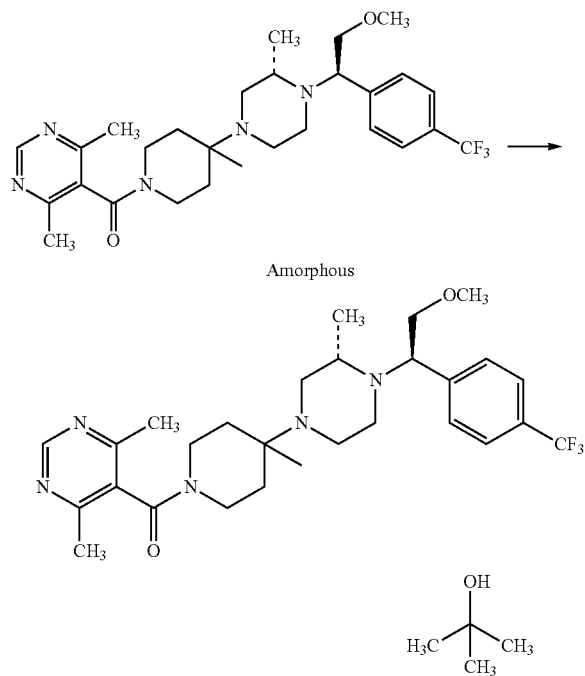

Amorphous Compound A was dissolved in tert-butanol. Partially crystalline material was obtained after lyophilization. Seeding a supersaturated tert-butanol solution of Compound A with the partially crystalline material precipitated a crystalline tert-butanol solvate, Solvate I.

An X-ray powder diffraction pattern was generated to characterize the tert-butanol solvate. The pattern, shown in FIG. 2, exhibited characteristic reflections corresponding to d-spacings as follows.

| Position [2Θ, °] | d-spacing [Å (Å = 0.1 nm)] | Relative Intensity [%] |
|---|---|---|
| 7.06 | 12.52 | 100 |
| 8.48 | 10.42 | 20 |
| 9.39 | 9.42 | 6 |
| 10.94 | 8.08 | 5 |
| 11.81 | 7.49 | 5 |
| 12.15 | 7.28 | 7 |
| 13.06 | 6.78 | 6 |
| 13.70 | 6.47 | 9 |
| 14.97 | 5.92 | 16 |
| 15.45 | 5.73 | 11 |
| 17.10 | 5.19 | 33 |
| 17.34 | 5.12 | 28 |
| 17.99 | 4.93 | 59 |
| 18.78 | 4.73 | 14 |
| 19.90 | 4.46 | 8 |
| 20.47 | 4.34 | 9 |
| 21.17 | 4.20 | 16 |
| 21.42 | 4.15 | 27 |
| 21.93 | 4.05 | 7 |
| 23.24 | 3.83 | 6 |
| 25.53 | 3.49 | 5 |

Example 3: Compound A Free Base Crystalline Anhydrate Form I

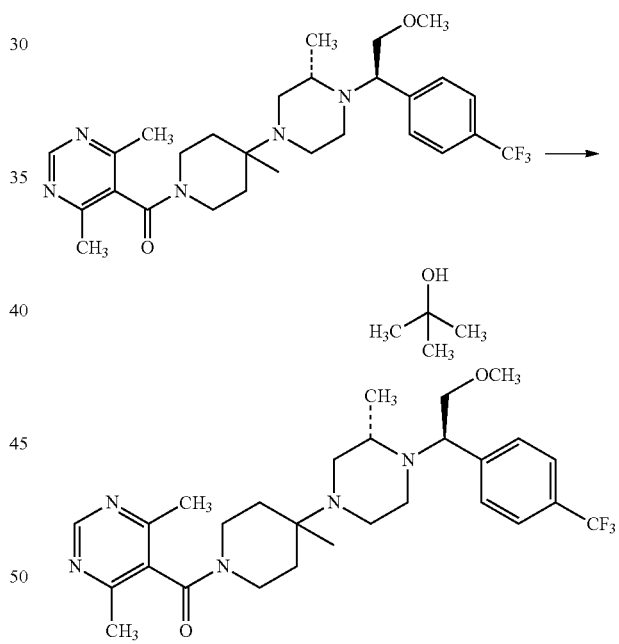

Method A

Tert-butanol solvate of Compound A, Solvate I, obtained from Example 2, dried in a vacuum oven under reduced pressure at 60° C. for at least ~15 h, yielded a crystalline solvent-free anhydrous form (Form I).

Method B 1.0 gram of Compound A tert-butanol solvate solids, Solvate I, obtained from Example 2, were dissolved in 3.0 ml of MeOH. 3.0 ml of water was added in portions; the solution was heated from 20° C. to 28° C. Form I seeds were introduced to the homogeneous solution. The crystallization proceeded slowly and additional water (~1.0 to 4.0 ml) was added to form a suspension. The mixture was aged for 30 h, yielding a crystalline anhydrate (Form 1).

3.15 grams of amorphous Compound A was dissolved in 15.8 ml EtOAc-heptane (1:4, v/v). Form I seeds were introduced and solution aged at 20° C. for 30 min. The mixture was cooled to 5° C. and held isothermally overnight yielding a crystalline anhydrate (Form 1).

An X-ray powder diffraction pattern was generated to characterize the crystalline anhydrate Form I. The pattern, shown in FIG. 3, exhibited characteristic reflections

| Position [2Θ, °] | d-spacing [Å (Å = 0.1 nm)] | Relative Intensity [%] |
|---|---|---|
| 5.06 | 17.47 | 4 |
| 7.01 | 12.60 | 6 |
| 9.69 | 9.13 | 7 |
| 9.85 | 8.98 | 5 |
| 10.24 | 8.64 | 29 |
| 10.99 | 8.05 | 9 |
| 11.34 | 7.80 | 44 |
| 12.48 | 7.09 | 61 |
| 13.55 | 6.53 | 17 |
| 13.89 | 6.38 | 11 |
| 14.17 | 6.25 | 100 |
| 15.10 | 5.87 | 30 |
| 15.93 | 5.56 | 30 |
| 16.62 | 5.34 | 9 |
| 17.33 | 5.12 | 72 |
| 18.07 | 4.91 | 8 |
| 18.32 | 4.84 | 16 |
| 18.68 | 4.75 | 8 |
| 18.93 | 4.69 | 27 |
| 19.41 | 4.57 | 18 |
| 19.57 | 4.54 | 16 |
| 19.90 | 4.46 | 48 |
| 20.15 | 4.41 | 30 |
| 20.69 | 4.29 | 18 |
| 21.14 | 4.20 | 33 |
| 21.35 | 4.16 | 24 |
| 22.00 | 4.04 | 6 |
| 22.27 | 3.99 | 23 |
| 22.77 | 3.91 | 8 |
| 24.05 | 3.70 | 6 |
| 24.55 | 3.63 | 6 |
| 24.88 | 3.58 | 7 |
| 25.10 | 3.55 | 8 |
| 27.58 | 3.23 | 6 |
| 27.84 | 3.20 | 5 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art, which are also intended to be encompassed by the following claims.

What is claimed is:

1. A compound that is a free base crystalline anhydrate form of:

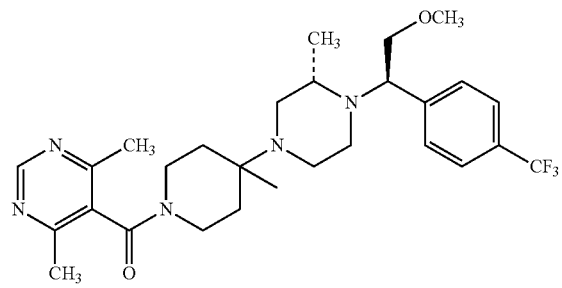 [SMILES: COC[C@@H](c1ccc(C(F)(F)F)cc1)N1CCN(C2(C)CCN(C(=O)c3c(C)ncnc3C)CC2)C[C@@H]1C]

characterized by an X-ray powder diffraction pattern obtained using copper Kα radiation, which comprises 2Θ values in degrees of about 5.06, 10.24, and 14.17.

2. The crystalline compound of claim 1 characterized by an X-ray powder diffraction pattern obtained using copper Kα radiation, which comprises 2Θ values in degrees of about 5.06, 10.24, 11.34, 12.48, 14.17, 17.33, 19.90, and 21.14.

3. The crystalline compound of claim 1 characterized by an X-ray powder diffraction pattern obtained using copper Kα radiation, which comprises 2Θ values in degrees of about 5.06, 10.24, 11.34, 12.48, 13.55, 14.17, 15.10, 15.93, 17.33, 18.32, 18.93, 19.41, 19.57, 19.90, 20.15, 20.69, 21.14, 21.35, and 22.27.

4. The crystalline compound of claim 1 characterized by an X-ray powder diffraction pattern obtained using copper Kα radiation, which comprises 2Θ values in degrees of about 5.06, 7.01, 9.69, 9.85, 10.24, 10.99, 11.34, 12.48, 13.55, 13.89, 14.17, 15.10, 15.93, 16.62, 17.33, 18.07, 18.32, 18.68, 18.93, 19.41, 19.57, 19.90, 20.15, 20.69, 21.14, 21.35, 22.00, 22.27, 22.77, 24.05, 24.55, 24.88, 25.10, 27.58, and 27.84.

5. The crystalline compound of claim 1 characterized by substantially the same powder X-ray diffraction pattern as shown in FIG. 3.

6. The crystalline compound of claim 1 in substantially pure form.

7. A composition of the compound

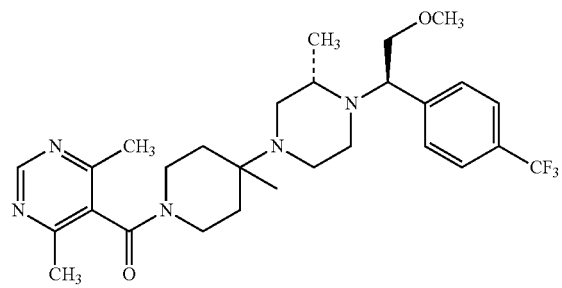 [SMILES: COC[C@@H](c1ccc(C(F)(F)F)cc1)N1CCN(C2(C)CCN(C(=O)c3c(C)ncnc3C)CC2)C[C@@H]1C]

wherein at least 75% of the total amount of the compound present is the free base crystalline anhydrate form of the compound of claim 1.

8. A composition of the compound

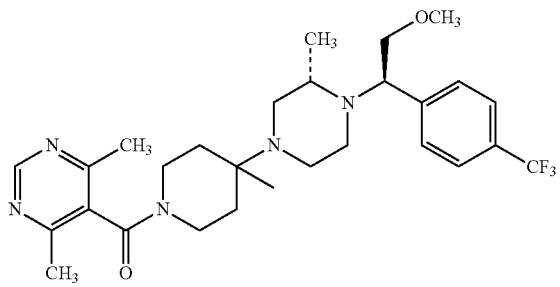

wherein about 94%-99% of the total amount of the compound present is the free base crystalline anhydrate form of the compound of claim 1.

9. A method for the treatment of infection by HIV or for the treatment of AIDS in a subject in need thereof which comprises administering to the subject an effective amount of the compound of claim 1.

10. A pharmaceutical composition comprising a therapeutically effective amount of the compound of claim 1 and a pharmaceutically acceptable carrier.

11. A method of making the compound of claim 1 comprising drying Compound A Solvate I under reduced pressure,
   wherein Compound A Solvate I is a crystalline tert-butanol solvate of the compound

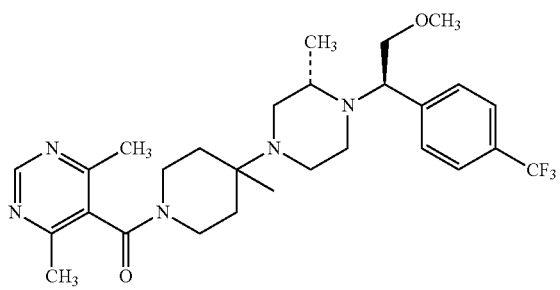

characterized by an X-ray powder diffraction pattern obtained using copper Kα radiation, which comprises 2Θ values in degrees of about 8.48, 9.39, and 17.10.

12. The method according to claim 11, further comprising making Compound A Solvate I by dissolving Compound A Amorphous Free Base in tert-butanol, and removing the tert-butanol solvent, wherein Compound A Amorphous Free Base is an amorphous free base form of the compound

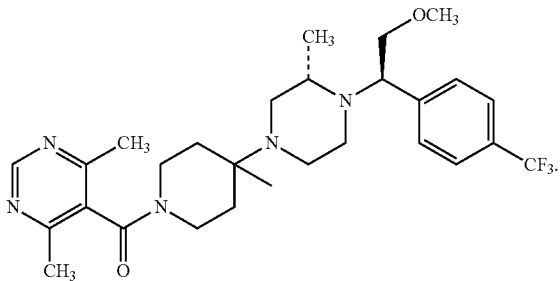 [SMILES: COC[C@@H](c1ccc(C(F)(F)F)cc1)N1CCN(C2(C)CCN(C(=O)c3c(C)ncnc3C)CC2)C[C@@H]1C]

13. The method according to claim 12, further comprising making Compound A Amorphous Free Base by treating the maleate salt of the compound

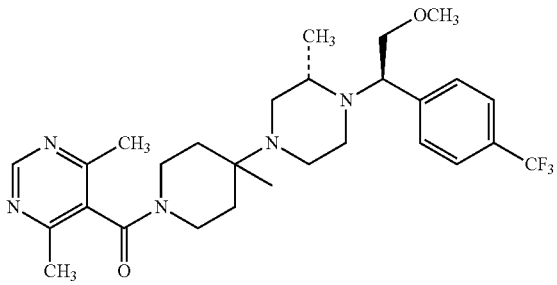 [SMILES: COC[C@@H](c1ccc(C(F)(F)F)cc1)N1CCN(C2(C)CCN(C(=O)c3c(C)ncnc3C)CC2)C[C@@H]1C]

with NaOH in dichloromethane.

14. A method of making the compound of claim 1 comprising dissolving Compound A Solvate I in methanol, adding water to the solution, and adding seeds of the compound of claim 1 to the solution to precipitate crystals of the compound of claim 1, wherein Compound A Solvate I is a crystalline tert-butanol solvate of the compound

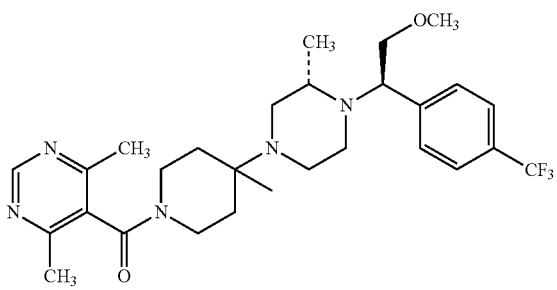 [SMILES: COC[C@@H](c1ccc(C(F)(F)F)cc1)N1CCN(C2(C)CCN(C(=O)c3c(C)ncnc3C)CC2)C[C@@H]1C]

characterized by an X-ray powder diffraction pattern obtained using copper Kα radiation, which comprises 2Θ values in degrees of about 8.48, 9.39, and 17.10.

15. The method according to claim 14, further comprising making Compound A Solvate I by dissolving Compound A Amorphous Free Base in tert-butanol, and removing the tert-butanol solvent,
   wherein Compound A Amorphous Free Base is an amorphous free base form of the compound

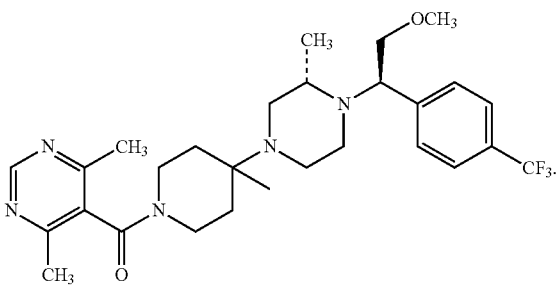 [SMILES: COC[C@@H](c1ccc(C(F)(F)F)cc1)N1CCN(C2(C)CCN(C(=O)c3c(C)ncnc3C)CC2)C[C@@H]1C]

16. The method according to claim 15, further comprising making Compound A Amorphous Free Base by treating the maleate salt of the compound

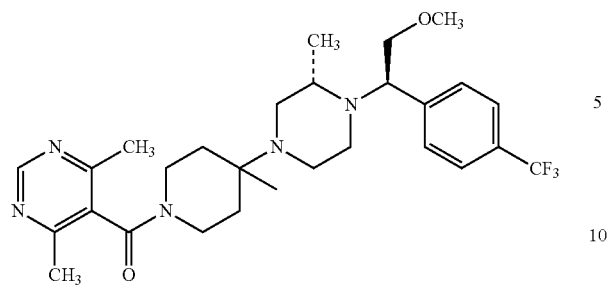
with NaOH in dichloromethane.
* * * * *